United States Patent [19]

Konrad et al.

[11] 4,450,103

[45] May 22, 1984

[54] PROCESS FOR RECOVERING HUMAN IFN-β FROM A TRANSFORMED MICROORGANISM

[75] Inventors: Michael W. Konrad, Alameda; Leo S. Lin, Fremont, both of Calif.

[73] Assignee: Cetus Corporation, Emeryville, Calif.

[21] Appl. No.: 353,360

[22] Filed: Mar. 1, 1982

[51] Int. Cl.[3] .......................... C07G 7/00; C12P 21/00; C12P 21/02; A61K 45/02

[52] U.S. Cl. .......................... 260/112 R; 260/112.5 R; 435/68; 435/70; 435/811; 424/85

[58] Field of Search .................... 260/112 R, 112.5 R; 435/68, 70, 811; 424/85

[56] References Cited

U.S. PATENT DOCUMENTS 4,289,689 9/1981 Friesen et al. .................. 260/112 R

FOREIGN PATENT DOCUMENTS 28033 5/1981 European Pat. Off. .
2068970 8/1981 United Kingdom .
2071108 9/1981 United Kingdom .

OTHER PUBLICATIONS

*Laboratory Text in Organic Chemistry,* Cason et al., Prentice-Hall, Inc., 1962, pp. 255-269.
Derynck et al.: Nature 287, 193 (1980).
Scandella et al.: Biochemistry 10, 4447 (1971).

*Primary Examiner*—Thomas G. Wiseman
*Assistant Examiner*—James Martinell
*Attorney, Agent, or Firm*—Albert P. Halluin; Thomas E. Ciotti; Janet E. Hasak

[57] ABSTRACT

A process for recovering IFN-β from transformed bacteria comprising: disrupting the cell membranes of the bacteria; solubilizing the IFN-β from the disruptate into an aqueous medium with a solubilizing agent such as sodium dodecyl sulfate; extracting the IFN-β from the aqueous medium with 2-butanol, 2-methyl-butanol, or mixtures thereof under conditions that maintain phase separation between the aqueous meduim and the extractant; and isolating the IFN-β from the extractant such as by precipitating the IFN-β from an aqeous buffer mixture of the extractant by lowering the pH thereof.

29 Claims, No Drawings

PROCESS FOR RECOVERING HUMAN IFN-β FROM A TRANSFORMED MICROORGANISM

DESCRIPTION

1. Technical Field

This invention is in the field of biochemical engineering. More particularly the invention concerns a biochemical separation or recovery process in which human IFN-β is separated or recovered from microorganisms that have been transformed to produce human IFN-β.

2. Background Art

Native human IFN-β is a glycoprotein having a reported molecular weight of 22,000–26,000 daltons. IFN-β, like other interferons, has been reported as having multiple biological effects including antiviral activity, cell growth or differentiation regulation, immune response modulation, and enzyme regulation. Native human IFN-β is produced by human fibroblasts, leukocytes or lymphoblastoid cells under induction by a variety of viral or nonviral inducers. One of the main methods currently used to produce native human IFN-β is to superinduce human fibroblast cultures with polyIC (polyriboinosinic acid: polyribocytidylic acid). IFN-β may be isolated from the cell secretions by gel chromotography and electrophoresis. This method is not currently viewed as a practical way of making the quantities of human IFN-β that will be required for large scale clinical testing and commercial distribution.

Genetic engineering offers an alternative method for making IFN-β. One recombinant method for producing IFN-β involves: (1) extracting polyadenylic acid (polyA)-rich 12S mRNA from virally induced human leukocytes; (2) using the mRNA as a template for synthesizing double-stranded cDNA; (3) cloning the cDNA into an appropriate vector; and (4) transforming *E. coli* with the vector. See also: European patent application No. 28033, published May 6, 1981; European patent application No. 32134, published July 15, 1981; European patent application No. 34307, published Aug. 26, 1981; and Belgian Pat. No. 837397, dated June 1, 1981 for techniques for producing human IFN-β.

Scandella and Kornberg, *Biochemistry* (1971) Vol 10: 4447–4456 describe the isolation of phospholipase from *E. coli* in which cell membranes were solubilized with sodium dodecyl sulfate (SDS) and 1-butanol was added to the solution to precipitate a portion of the protein solubilized by the SDS. Derynck, et al., *Nature* (1980) 287: 193–197 report lysing *E. coli* cells that had been transformed with IFN gene-containing plasmids by heating the cells in one % SDS, one % 2-mercaptoethanol, 5 M urea. The S100 extract of the lysate was reported to have interferon activity. Compositions containing SDS have also been used to stabilize the biological activity of interferons. See U.S. Pat. No. 3,981,991.

The above described art does not teach or suggest a process for recovering human IFN-β from transformed microorganisms that is adaptable to practical production of the quantities of human IFN-β required for clinical testing and eventual commercial distribution. A principal object of the present invention is to provide such a process.

DISCLOSURE OF THE INVENTION

The invention is a process for extracting human IFN-β solubilized with an appropriate solubilizing agent from an aqueous medium comprising contacting the aqueous medium containing the human IFN-β with an organic extractant having the formula:

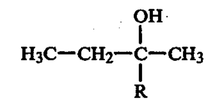

where R is hydrogen or methyl.

A preferred embodiment of the invention process involves human IFN-β solubilized with SDS and isolates the human IFN-β from the extract by precipitating the human IFN-β from the extract by lowering its pH.

MODES FOR CARRYING OUT THE INVENTION

As used herein the term "IFN-β" is synonomous with the term "fibroblast interferon."

As used herein the term "human IFN-β" denotes IFN-β that is produced by microorganisms that have been transformed with a human IFN-β gene or a human interferon gene that expresses an interferon whose amino acid sequence is the same as or substantially homologous to native human IFN-β. Such interferons include unglycosylated interferons, interferons lacking terminal methionine groups, and hybrid interferons having physical and chemical properties (e.g., hydrophobicity, solubility, stability) that are substantially similar to nonhybrid species of IFN-β.

As used herein the term "transformed microorganism" denotes a microorganism that has been genetically engineered to produce human IFN-β. Examples of transformed microorganisms are described in the patent publications referred to in Background Art, supra and in the examples of this application. Bacteria are preferred microorganisms for use in the invention. *E. coli* is particularly preferred.

The transformed microorganisms are grown in a suitable growth medium, typically to an optical density (O.D.) of at least about 10 at 680 nm, and preferably between about 50 and 100 at 680 nm. The composition of the growth medium will depend upon the particular microorganism involved. The medium is an aqueous medium containing compounds that fulfill the nutritional requirements of the microorganism. Growth media will typically contain assimilable sources of carbon and nitrogen, energy sources, magnesium, potassium and sodium ions, and optionally amino acids and purine and pyrimidine bases. Review of Medical Microbiology, Lange Medical Publications, 14th Ed pp 80–85 (1980). Growth media for *E. coli* are well known in the art. Depending upon the particular solubilizing agent used in the invention process it may be desirable to minimize the amount of substances in the growth medium that may decrease the solubility of the agent in water. For instance, potassium ions affect the solubility of SDS and, therefore, should be kept at a minimum when SDS is used as a solubilizing agent in the process.

Once the culture has reached the desired cell density, the cells are optionally killed by heating or adding a cytotoxic agent, such as chloroform or toluene, to the medium that may be removed easily after the cells have been killed. The cells are thereafter concentrated, if necessary, to about 20 to 150 mg/ml, preferably 80 to 100 mg/ml (O.D. 40 to 300, preferably 160 to 200 at 680 nm) by filtration, centrifugation, or other conventional methods. The concentration step is also optional.

Following concentration the cell membranes of the microorganisms are disrupted. The main purpose of disruption is to facilitate the following solubilization of the particulate matter in the concentrate. In this regard bioactivity assays indicate that much of the interferon is associated with (i.e., contained in or bound to) the cell membrane. Accordingly, disruption of the cell membrane enhances the contact of the solubilizing agent with the membranes and thus increases the rate at which the interferon associated with the membrane goes into solution. Conventional cell disruption techniques such as homogenization, sonication, or pressure cycling may be used in this step of the process. A preferred method is to pressure cycle the cell suspension up to about $3.4\times10^4$ to $1\times10^5$ kPa. The cells disrupt due to the sudden decrease in pressure. Either before or after the disruption, the pH of the liquid phase of the concentrate or disruptate, as the case may be, is adjusted, if necessary, to a level that facilitates dissolution of the solubilizing agent and the particulate matter in the concentrate/disruptate. The pH may be so adjusted by adding suitable buffers. In most instances pHs in the range of about 7 to about 8 will be used.

After the cells have been disrupted the particulate matter may be separated from the liquid phase of the disruptate and resuspended in an aqueous medium buffered to the optimal pH for the solubilization. In any event, the protein concentration of the cell suspension pension subjected to solubilization will usually be in the range of about 2 to about 15 mg/ml, preferably 6 to 8 mg/ml.

The solubilization of the particulate cellular material, including the human IFN-β component thereof, may be carried out concurrently with the disruption or sequentially following the disruption. It is preferably carried out as a separate step following the disruption. The solubilization is preferably carried to completion—that is, substantially all of the particulate matter (e.g. protein, lipids, nucleic acid, phospholipids) in the disruptate is dissolved into the aqueous medium. Substantially complete dissolution of the particulate matter is achieved by adding an appropriate solubilizing agent to the aqueous suspension. Surface active agents (detergents) that have a suitable hydrophobic-hydrophilic balance to solubilize human IFN-β and that form a complex with human IFN-β that can be extracted into the organic phase may be used in the invention. Strong natural or synthetic anionic surface active agents, such as alkali metal salts of fatty acids and alkali metal alkyl sulfates, may be used. Such agents will usually contain 10 to 14 carbon atoms. SDS and sodium laurate are particularly preferred solubilizing agents. Examples of other solubilizing agents that may be used in the process are sodium dodecyl sulfonate, sodium decyl sulfate, sodium tetradecyl sulfate, sodium tridecyl sulfonate, sodium myristate, sodiumn caprate, sodium dodecyl N-sarcosinate, and sodium tetradecyl N-sarcosinate.

The amounts of solubilizing agent used in the solubilization will depend upon the particular agent and the amount of protein to be solubilized. In most instances agent:protein weight ratios in the range of about 1:1 to 10:1 will be sufficient. When SDS is used an SDS:protein ratio of about 1:1 to about 5:1, preferably about 3:1, will be used. Temperatures in the range of 15° C. to 60° C. will normally be used in the solubilization. Mixing will typically be used to enhance contact between the solution and particulate matter and thus decrease the time it takes to dissolve the cellular matter. The solubilization is considered complete when the solution is substantially clear. ODs of less than about 0.4 at 280 nm are characteristic of the solubilization end point.

Following the solubilization the ionic strength of the solution is adjusted, if necessary, to a level at which the solution and organic extractant will be substantially immiscible. The ionic strength will be in the range of 0.05 to 0.15. Inorganic salts, such as NaCl, may be added to the solution for this purpose. Such ionic strengths enable phase separation after the extraction. The extractants used in the process are 2-butanol, 2-methyl-2-butanol, or mixtures thereof. The mixtures preferably contain less than about 50% by volume 2-methyl-2-butanol. 2-butanol is a preferred extractant. The ability of these alcohols to extract human IFN-β from the solubilizate is specific. Homologous alcohols were found to be ineffective extractants. The extractant will normally be combined with the aqueous solution of human IFN-β in volumes ratios in the range of about 0.8:1 to about 3:1, preferably about 1:1 (extractant:aqueous solution). The extraction may be carried out using conventional batch or continuous liquid-liquid extraction techniques and equipment. The extraction will normally be carried out at 20° C. to 100° C. and involve contact times in the range of about one minute to one hr. The optimum contact time will depend upon the particular solubilizing agent:extractant combination. When SDS is used, shorter times in the above range may be used. When sodium laurate is used, longer times in the range must be used. The pH of the extraction mixture will range between about 6 and 9, with a pH of about 7.5 being preferred when SDS is used and a pH of about 8.5 when sodium laurate is used.

Upon completion of the extraction the aqueous phase and extractant phase are separated and the human IFN-β is isolated from the extractant phase. The particular isolation procedure used will depend upon the solubilizing agent involved and the desired degree of purity of the final product. Various isolation techniques such as precipitation, molecular sieve chromotography, affinity chromotography, and electrophoresis may be employed. In instances in which SDS has been used, the IFN-β together with other proteins may be precipitated from the extractant mixed with aqueous buffer at vol ratios of about 2.5:1 to about 5:1, preferably about 3:1, by reducing the pH, typically to below about 5. Separation of the precipitate from the supernatant and evaporation of residual extractant from the precipitate provide a product that is greater than about 95% pure protein. This product also contains minor amounts of nucleic acids (<1% to 2% by weight) and SDS (<1% w/v). SDS may be removed if desired, by electrodialysis using the methodology of Tuszenski and Warren, Anal Biochem (1975) Vol. 67. When sodium laurate is used as a solubilizing agent it will precipitate from the extractant together with the protein on lowering the pH. The sodium laurate may be extracted from the protein using solvents such as acetone or methanol.

The thus isolated human IFN-β may be lyophilized or put into solution pending use. Nontoxic, nontherapeutic, nonimmunogenic stabilizers may be added to the IFN-β if desired. Diluents that may be used in the solutions may be selected from aqueous based vehicles commonly used to formulate pharmaceuticals for injection. The diluent should, of course, not affect the biological activity of the IFN-β. Examples of such diluents are saline, Ringer's solution, dextrose solution, and Hank's solution. The same diluents may be used to reconstitute lyophilized human IFN-β.

The invention process is further described by the following examples. These examples are not intended to limit the invention in any manner.

EXAMPLE 1

Human IFN-β was recovered from *E. coli* that had been transformed to produce human IFN-β. The *E. coli* were grown in the following growth medium to a cell density (O.D.) of 10–11 at 680 nm (dry wt 8.4 g/l).

| Ingredient | Concentration |
|---|---|
| $NH_4Cl$ | 20 μM |
| $K_2SO_4$ | 16.1 μM |
| $KH_2PO_4$ | 7.8 μM |
| $Na_2HPO_4$ | 12.2 μM |
| $MgSO_4.7H_2O$ | 3 μM |
| $Na_3$ citrate.$2H_2O$ | 1.5 μM |
| $MnSO_4.4H_2O$ | 30 μM |
| $FeSO_4.7H_2O$ | 30 μM |
| $CuSO_4.5H_2O$ | 3 μM |
| L-tryptophan | 70 mg/l |
| $FeSO_4.7H_2O$ | 72 μM |
| thiamine.HCl | 20 mg/l |
| tetracycline | 10 mg/l |
| glucose | 40 g/l |

pH control with $NH_4OH$

A 9.9 l (9.9 kg) harvest of the transformed *E. coli was cooled to* 20° C. and concentrated by passing the harvest through a cross-flow filter at an average pressure drop of 16 psi and steady state filtrate flow rate of 260 ml/min until the filtrate weight was 8.8 kg. The concentrate (approximately one liter) was drained into a vessel and cooled to 15° C. The cells in the concentrate were then disrupted by passing the concentrate through a Manton-Gaulin homogenizer at 5° C., 10,000 psi. The homogenizer was washed with one liter phosphate buffered saline, pH 7.4 (PBS), and the wash was added to the disruptate to give a final volume of two liters. This volume was continuously centrifuged at 12000×g at a 50 ml/min flow rate. The solid was separated from the supernatant and resuspended in four liters PBS containing two % by wt SDS. This suspension was stirred at room temperature for 15 min after which there was no visible suspended material. The solution was then extracted with 2-butanol at a 1:1 2-butanol:solution volume ratio. The extraction was carried out in a liquid-liquid phase separator using a flow rate of 200 ml/min. The organic phase was then separated and evaporated to dryness to yield 21.3 g of protein. This was resuspended in distilled water at a 1:10 volume ratio.

The recovered product was assayed for human IFN-β using an assay based on protection against viral cytopathic effect (CPE). The assay is made in microtiter plates. Fifty μl of minimum essential medium are charged into each well and 25 μl of the sample is placed in the first well and 1:3 volume dilutions are made serially into the following wells. Virus (vesicular stomatitis), cell (human fibroblast line GM-2504), and reference IFN-β controls are included on each plate. The reference IFN-β is 100 units per ml. The plates are then irradiated with UV light for 10 min. After irradiation 100 μl of the cell suspension ($1.2\times10^5$ cells/ml) is added to each well and the trays are incubated for 18–24 hr. A virus solution at one plaque-forming unit per cell is added to each well except the cell control. the trays are then incubated until the virus control shows 100% CPE. This normally occurs 18–24 hr after adding the virus solution. Assay results are interpreted in relation to the location of the 50% CPE well of the reference IFN-β control. From this point the titer of interferon for all samples on the plate are determined. The activity of the recovered product was determined to be $2.9\times10^6$ U/mg.

EXAMPLE 2

Partial purifications of human IFN-β using SDS as a solubilizing agent and 2-butanol, 2-methyl-2-butanol or various mixtures thereof as an extractant were made. Purifications using other alcohols were also attempted. The procedure used in these purifications was as follows.

The *E. coli* cells, 1.3 g (wet weight), were suspended in 10 ml of 1% SDS (wt/vol) in 0.1 M PBS, pH 7.4. The suspension was sonicated until it was clear. An equal volume of extractant was added to the sonicate, mixed, and centrifuged at 7000×g for 10 min at ambient temperature. The extractant and aqueous phases were separated and the extractant phase was assayed for human IFN-β using the assay referred to in Example 1. The following table presents the results of those assays.

TABLE 1

| Organic Solvent | Human Fibroblast Interferom Anti-Viral Activity $\log_{10}$ Units |
|---|---|
| Phosphate Buffered Saline (PBS), 1% Sonicate (Starting Materials) | 6.0 |
| 2-Butanol (2BuOH) | 5.5 |
| n-Pentanol | 3.5 |
| 2-Pentanol | 2.8 |
| 1-Pentanol | <1 |
| 2-Me—1-butanol | <1 |
| 3-Me—1-butanol | <1 |
| 2-Et—1-butanol | <1 |
| 2-Me—2-butanol | 5.0 |
| 1-Butanol | <1 |
| 2-Me—1-pentanol | <1 |
| 1-Hexanol | <1 |
| 2-Et—1-Heptanol | <1 |
| 1-Heptanol | <1 |
| 1-Octanol | <1 |
| 2-Octanol | <1 |
| Toluene | <1 |
| 75% 2-BuOH/25% 2-Me—2-butanol (vol/vol) | 5.5 |
| 50% 2-BuOH/50% 2-Me—2-butanol (vol/vol) | 5.5 |
| 25% 2-BuOH/75% 2-Me—2-butanol (vol/vol) | 5.0 |

The data of the foregoing table show the specificity of 2-butanol and 2-methyl-2-butanol in the process. The data indicate that homologous alcohols such as 1-butanol, 2-methyl-1-butanol, and 1-pentanol, are ineffective extractants in the process.

EXAMPLE 3

A 10 l tank was harvested (9.8 kg) and concentrated to 2.2 liters by cross-flow filtration. The slurry was frozen and stored for 34 days and then thawed.

The thawed concentrate was disrupted by 3 passes at $7\times10^4$ kPa in a Manton-Gaulin homogenizer. The disruptate was collected and made to 4 liters with a solution of sodium laurate to give a final concentration of 1% w/v laurate. The pH was adjusted to 8.5 with 10% NaOH. The solution was contacted with a mixture of 50 vol% 2-butanol and 50 vol% 2-methyl-2-butanol in a static mixer. The emulsion was pumped into a holding tank and agitated to give a contacting time of 15 minutes. This emulsion was separated as in Example 1 and the IFN-β recovered in the organic phase. The activity recovered was 16% of initial with a specific activity (determined as in Example 1) of $3.7\times10^5$ U/mg protein.

EXAMPLE 4

The process of Example 1 was repeated except that after extraction and separation of the aqueous and organic phases and mixing of the organic phase with PBS at a volume ratio of 3:1 the pH of the mixture was lowered to about 5 by addition of glacial acetic acid. The resulting precipitate was separated by centrifugation at 10000–17000×g for 15 min and the pellet was redissolved in 10% w/v SDS.

The precipitate was applied to a molecular sieve column with a Sepacryl S-200 Superfine (Pharmacia) matrix. The column was equilibrated with 50 mM sodium acetate buffer, pH 5.5 containing 2 mM dithiothreitol and 0.1% SDS (w/v). The column was developed with the same buffer at a flow rate of 15.6 ml per $cm^2$ per hour. Protein profile was monitored at 280 nm with a UV spectrophotometer. Fractions collected were assayed for protein content by the method of Lowry. Interferon concentration was determined by the CPE assay described in Example 1. Degree of interferon purity was determined by SDS polyacrylamide gel electrophoresis (Laemmle, Nature 1970). Fractions containing highest interferon activities were pooled and the specific activity of the pooled interferon preparation was determined to be $1-2\times10^7$ international units per mg protein.

Modifications of the above described modes for carrying out the invention that are obvious to those of ordinary skill in the biochemical engineering field or related technologies are intended to be within the scope of the following claims.

We claim:

1. A process for extracting unglycosylated human IFN-β solubilized with an appropriate solubilizing agent from an aqueous medium comprising contacting the aqueous medium containing the unglycosylated human IFN-β with an organic extractant of the formula

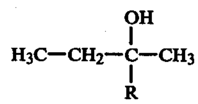

where R is hydrogen or methyl under conditions wherein an aqueous and an organic phase are formed.

2. The process of claim 1 wherein the solubilizing agent is an anionic surface active agent.

3. The process of claim 1 wherein the solubilizing agent is sodium dodecyl sulfate or sodium laurate.

4. The process of claim 1 wherein the contacting is carried out under conditions that facilitate phase separation between the aqueous phase and the extractant phase.

5. The process of claim 1 wherein the ionic strength of the aqueous medium is about 0.05 to about 0.15.

6. The process of claim 1 wherein the ionic strength is provided by sodium chloride.

7. The process of claim 1, 2, 3, or 4 wherein the extractant is 2-butanol.

8. The process of claim 1, 2, 3, or 4 including the step of isolating the unglycosylated human IFN-β from the extractant.

9. A process for recovering unglycosylated human IFN-β from a transformed microorganism containing unglycosylated human IFN-β comprising:

(a) disrupting the cell membrane of the microorganism;

(b) solubilizing the unglycosylated human IFN-β in the disruptate into an aqueous medium with a solubilizing agent that forms an extractable complex with the unglycosylated human IFN-β;

(c) extracting the complex from the aqueous medium with an organic extractant of the formula

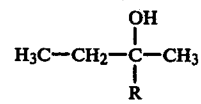

where R is hydrogen or methyl; and (d) isolating the unglycosylated IFN-β from the extract.

10. The process of claim 9 wherein the microorganism is a bacterium.

11. The process of claim 10 wherein the microorganism is *E. coli*.

12. The process of claim 9 or 11 wherein the microorganism is contained within a fermentation medium and is concentrated before step (a).

13. The process of claim 9 or 11 wherein the disruption is effected by subjecting the microorganism to pressure cycling to rupture its cell membrane.

14. The process of claim 9 wherein the solubilization of step (b) dissolves substantially all the particulate matter in the disruptate.

15. The process of claim 9 or 14 wherein the pH of the aqueous medium is one that maintains the solubilizing agent in solution.

16. The process of claim 9 wherein the solubilizing agent is an anionic surface active agent.

17. The process of claim 9 wherein the solubilizing agent is an alkali metal alkyl sulfate or an alkali metal salt of a fatty acid wherein said sulfate or said salt contains 10 to 14 carbon atoms.

18. The process of claim 15 wherein the anionic surface active agent is sodium dodecyl sulfate or sodium laurate.

19. The process of claim 15 wherein the pH is about 7 to about 8.

20. The process of claim 16 wherein the surface active agent is sodium dodecyl sulfate and the weight ratio of sodium dodecyl sulfate to protein in the aqueous medium is in the range of about 1:1 to about 5:1.

21. The process of claim 9 wherein the weight ratio is about 3:1.

22. The process of claim 9 wherein the extraction is carried out under conditions that facilitate phase separation between the aqueous phase and the extractant phase.

23. The process of claim 22 wherein the ionic strength of the aqueous medium is about 0.05 to about 0.15.

24. The process of claim 23 wherein said ionic strength is provided by sodium chloride in the aqueous medium.

25. The process of claim 9, 22, 23, or 24 wherein the organic extractant is 2-butanol.

26. The process of claim 9 wherein the isolation includes:

(i) mixing the extract with an aqueous buffer;

(ii) precipitating the unglycosylated human IFN-β from the mixture of (i) by lowering the pH of the mixture; and (iii) isolating the precipitated unglycosylated human IFN-β from the supernatant.

27. The process of claim 26 wherein the pH is lowered to below about 5.

28. The process of claim 26 or 27 wherein the solubilizing agent is sodium dodecyl sulfate.

29. A process for recovering unglycosylated human IFN-β from transformed *E. coli* bacteria containing unglycosylated human IFN-β said bacteria being contained in a fermentation medium comprising:

(a) concentrating said bacteria in the fermentation medium;

(b) disrupting the cell membrane of the bacteria by subjecting the bacteria to pressure cycling;

(c) separating the solid cellular material from the remainder of the disruptate;

(d) suspending the cellular material in an aqueous medium at a protein concentration in the range of 2 to 15 mg/ml and a pH in the range of about 7 and 8;

(e) solubilizing the cellular material with sodim dodecyl sulfate at a sodium dodecyl sulfate:protein weight ratio of about 1:1 to 1:5;

(f) extracting the unglycosylated human IFN-β from the aqueous medium with 2-butanol wherein the ionic strength of the aqueous medium is sufficient to maintain the aqueous medium and 2-butanol substantially immiscible;

(g) separating the aqueous phase from the unglycosylated, human IFN-β-containing 2-butanol phase; and (h) precipitating the human IFN-β from the 2-butanol phase by mixing the 2-butanol phase with an aqueous buffer and lowering the pH of the mixture to below about 5.

* * * * *